(12) United States Patent
Reed

(10) Patent No.: US 8,986,269 B2
(45) Date of Patent: Mar. 24, 2015

(54) WOUND LEAKAGE VACUUM COLLECTION DEVICE

(75) Inventor: Michael Clark Reed, Casper, WY (US)

(73) Assignee: UlceRx Medical Inc., San Jose, CA (US)

( * ) Notice: Subject to any disclaimer, the term of this patent is extended or adjusted under 35 U.S.C. 154(b) by 0 days.

(21) Appl. No.: 12/944,705

(22) Filed: Nov. 11, 2010

(65) Prior Publication Data

US 2012/0123359 A1 May 17, 2012

(51) Int. Cl.
*A61M 1/00* (2006.01)
*A61F 13/00* (2006.01)
*A61M 27/00* (2006.01)
*A61F 13/02* (2006.01)
*A61L 15/60* (2006.01)

(52) U.S. Cl.
CPC .............. *A61M 1/008* (2013.01); *A61M 27/00* (2013.01); *A61M 1/0049* (2013.01); *A61M 1/0088* (2013.01); *A61M 1/0023* (2013.01); *A61M 1/0001* (2013.01); *A61M 1/0066* (2013.01); *A61M 1/0011* (2013.01); *A61M 2205/7536* (2013.01); *A61F 13/00068* (2013.01); *A61F 13/0209* (2013.01); *A61F 2013/0054* (2013.01); *A61F 2013/00536* (2013.01); *A61L 15/60* (2013.01); *Y10S 604/902* (2013.01)
USPC ........... 604/319; 604/305; 604/313; 604/543; 604/540; 604/541; 604/902

(58) Field of Classification Search
CPC ............ A61M 1/0049; A61M 1/0088; A61M 1/0023; A61M 1/0001; A61M 1/0066; A61M 1/0011; A61M 27/00; A61M 2205/7536; A61M 2001/0092; A61F 13/00068; A61F 13/0209; A61F 2013/0054; A61F 2013/00536; A61L 15/60; Y10S 604/902
USPC ................. 604/319, 305, 313, 543, 540, 541
See application file for complete search history.

(56) References Cited

U.S. PATENT DOCUMENTS

| | | | |
|---|---|---|---|
| 5,980,507 A * | 11/1999 | Fassuliotis et al. | 604/540 |
| 6,648,862 B2 * | 11/2003 | Watson | 604/319 |
| 6,942,634 B2 * | 9/2005 | Odland | 604/6.09 |
| 7,503,910 B2 | 3/2009 | Adahan | |
| 7,553,306 B1 * | 6/2009 | Hunt et al. | 604/543 |
| 8,021,348 B2 | 9/2011 | Risk, Jr. et al. | |
| RE42,834 E | 10/2011 | Watson | |
| 8,251,979 B2 | 8/2012 | Malhi | |
| 8,267,908 B2 | 9/2012 | Coulthard | |
| 8,303,555 B2 | 11/2012 | Miau et al. | |
| 2008/0082059 A1 * | 4/2008 | Fink et al. | 604/305 |
| 2008/0234641 A1 * | 9/2008 | Locke et al. | 604/313 |
| 2009/0012484 A1 * | 1/2009 | Nielsen et al. | 604/319 |

(Continued)

FOREIGN PATENT DOCUMENTS

EP 387329 B1 * 1/1996

OTHER PUBLICATIONS

International Search Report, International Searching Authority, Feb. 21, 2012, pp. 1-14.

*Primary Examiner* — Tatyana Zalukaeva
*Assistant Examiner* — Andrew J Mensh
(74) *Attorney, Agent, or Firm* — E. Thomas Wheelock

(57) ABSTRACT

A wound leakage collection device is described wherein a chamber provides a volume wherein wound leakage material can be removed from vacuum tubing and said device can be easily removed from a wound and a negative pressure source.

37 Claims, 3 Drawing Sheets

(56) References Cited

U.S. PATENT DOCUMENTS

| | | |
|---|---|---|
| 2009/0204085 A1* | 8/2009 | Biggie et al. ............... 604/313 |
| 2009/0312725 A1* | 12/2009 | Braga ....................... 604/313 |
| 2010/0125258 A1 | 5/2010 | Coulthard |
| 2010/0145289 A1* | 6/2010 | Lina et al. .................. 604/319 |
| 2010/0324510 A1* | 12/2010 | Andresen et al. ........... 604/319 |
| 2011/0137267 A1* | 6/2011 | Phillips et al. .............. 604/290 |
| 2013/0304004 A1 | 11/2013 | Riesinger |

* cited by examiner

WOUND LEAKAGE VACUUM COLLECTION DEVICE

FIELD OF THE INVENTION

This invention relates generally to capture wound leakage material that is drawn away from the vicinity of a wound using a vacuum line.

BACKGROUND OF THE INVENTION

Negative pressure wound therapy enhances wound healing in multiple ways, including, but not limited to, micro-stimulation of granulation, macro-mechanical holding, stimulation of blood flow, reduction of edema, and removal of healing inhibitory enzymes and wound contaminants. One consequence of providing the negative pressure therapy is a need to collect and remove the drainage. It is sometimes the case that severe wounds leak significant amounts of byproduct material. It is advantageous to remove the wound leakage material or wound byproduct material via a vacuum or negative pressure system. It is typical that negative pressure wound dressings are changed one to four times a week. However, the collection canister employed may need to be changed more or less often, depending on the amount of wound leakage material drainage amounts, which differs greatly from wound to wound.

In the wound treatment art, a vacuum or negative pressure source is in contact with a wound via a vacuum tube line, a wound tape material making contact between the wound and the vacuum tube line, and a reservoir canister to hold the byproduct material.

Often the reservoir canister is attached to the negative pressure system. The reservoir has to be monitored such that byproduct material, typically a liquid, does not flow into the mechanical vacuum or negative pressure device. The reservoir canister often encompasses a large portion of the vacuum or negative pressure device. The combination of reservoir canister and vacuum device is often too bulky and cumbersome to be carried easily by the patient during activities of daily living. Such bulky vacuum units make the patient less inclined to complete a treatment regimen.

Other means of removing wound leakage material include applying an absorbent material next to the wound. Once the absorbent material has reached saturation of wound leakage material, the absorbent material must be removed. Another absorbent material must be placed next to the wound to further remove wound leakage material until the wound is a fully drained. The process of redressing a wound to further eliminate wound leakage material is often messy and involves the use of additional materials. Patients are most often unable or unwilling to undertake the required dressing changes. If dressing is not changed properly, there is an elevated risk of infection and wound healing complication for the patient.

Both of the methods described above, as well as others, require significant amounts of material, equipment or effort to effectively drain a healing wound.

SUMMARY OF THE INVENTION

Accordingly, it is an object of the present invention to provide an inline vacuum wound leakage collection device to remove wound leakage material. Additional objects, advantages and novel features of the invention will be set forth in part in the description which follows, and in part will become apparent to those skilled in the art upon examination of the following or may be learned by practice of the invention. The objects and advantages of the invention may be realized and attained by means of the instrumentalities and combinations particularly pointed out in the appended claims.

To achieve the foregoing and other objects, and in accordance with the purposes of the present invention, as embodied and broadly described herein, the wound leakage collection device hereof includes vacuum tubing having a wall, the wall having an external surface, an internal surface, a first end in fluid communication with a source of negative pressure, a second end in fluid communication with a source of wound leakage, and a portion between the first end and the second end having one or more perforation through the wall thereof; a chamber for enclosing and maintaining a vacuum around the external surface of the perforated portion of the tubing; absorbent material disposed within the chamber adjacent to the external surface of the perforated portion of the tubing; and one or more vapor-permeable plug disposed in the internal surface of the vacuum tubing between the first end and the perforated portion thereof.

In another embodiment of the present invention, and in accordance with its objects and purposes, a method for containing leakage from a wound is presented. The method comprising the steps applying a vacuum from a source of negative pressure to one end of a tube, the other end thereof being in fluid communication with a source of wound leakage; collecting wound leakage from the tube through one or more perforation in a portion of the wall of the tube into absorbent material disposed in a chamber enclosing and maintaining a vacuum around the external surface of the perforated portion of the tube; and blocking wound leakage from entering the source of negative pressure using one or more vapor-permeable plug disposed within the tube between the one or more perforation and the source of negative pressure.

Benefits and advantages of the present invention include, but are not limited to, providing a less cumbersome device and a more advantageous and cleaner wound treatment by reducing the accumulation of wound byproducts from a wound.

BRIEF DESCRIPTION OF THE DRAWINGS

The invention can be best understood by those having ordinary skill in the art by reference to the following detailed description when considered in conjunction with the accompanying drawings in which.

DETAILED DESCRIPTION OF THE INVENTION

Figure 1:
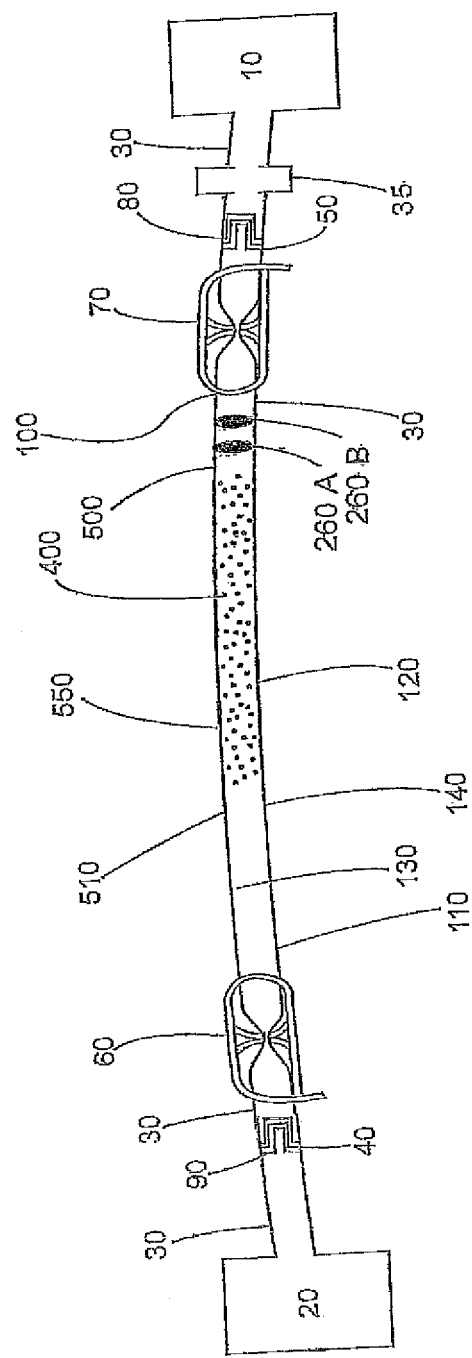
FIG. 1 illustrates a side view of an embodiment of vacuum tubing portion of the invention.

Reference will now be made in detail to embodiments of the invention, examples of which are illustrated in the accompanying drawings. Throughout the following detailed description, the same reference characters refer to the same or similar elements in all figures.

Referring to FIG. 1, a side view of one embodiment of the present invention is shown. The negative pressure source 10 typically is disposed opposite the wound leakage material source 20, and is connected thereto via the vacuum tubing 30.

The vacuum tubing comprises a first end 100, a second end 110 and an intermediate portion 120. The intermediate portion 120 comprises a wall 550 having one or more perforations 400 therethrough, a first end 500 and a second end 510. The vacuum tubing further comprises an internal surface 130 and an external surface 140. The one or more perforations 400 provide for the flow of wound leakage material from the internal surface 130 to the external surface 140 of the wall 550.

FIG. 1 also depicts the one or more plugs 260A and 260B filling the vacuum tubing 30 and contacting with the internal surface 130. The one or more plugs 260A and 260B are disposed between the first end 500 of the intermediate portion 120 and the first end 100 of the vacuum tubing 30. The one or more plugs 260A and 260B are comprised of vapor-permeable material. In one embodiment of the invention, the one or more plugs 260A and 260B comprise a material that is liquid impermeable.

FIG. 1 illustrates a vacuum gauge 35, which monitors pressure in the vacuum tubing 30 to allow for effective wound therapy. FIG. 1 depicts a first vacuum line connector 50 disposed between the one or more plugs 260A and 260B and the negative pressure source 10. The vacuum line connector 50 connects to a vacuum line connector 80 attached to the vacuum tubing 30. FIG. 1 further depicts a second vacuum line connector 40 between the second end of the vacuum tubing 110 and the wound leakage source 20. The vacuum line connector 40 connects to a vacuum line connector 90 attached to the vacuum tubing 30. The vacuum line connectors 50 and 40 allow for quick and easy removal and replacement of the wound leakage collection device.

FIG. 1 depicts a first tubing clamp 70 between the one or more plugs 260 and the first vacuum line connector 50. FIG. 1 further depicts a second clamp 60 between the second end portion 510 of the intermediate portion 120 and the second vacuum line connector 40. The clamps 70 and 60 allow for isolation and containment of wound leakage material during removal and replacement of the wound leakage collection device.

Figure 2:
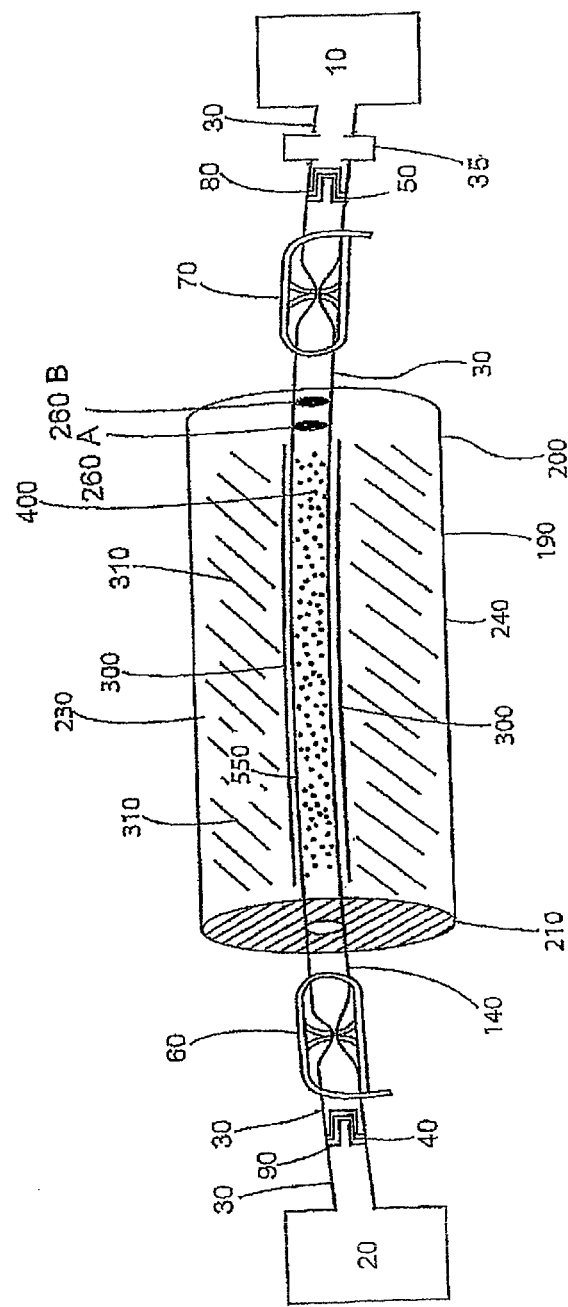
FIG. 2 illustrates a side view of an embodiment of the fluid absorption chamber of the present invention including the vacuum line portion and the chamber portion sealed to the vacuum line portion shown in FIG. 1 hereof, forming thereby a removable wound leakage material collection device.

FIG. 1 and FIG. 2 depict the clamps closed; however, during collection of wound leakage material, the clamps 70 and 60 would be open to maximize the fluid flow and pressure (vacuum) differential between the negative pressure source 10 and the wound leakage source 20.

FIG. 2 depicts the chamber 190 surrounding the wall 550 of the wound leakage material collection device. The chamber 190 comprises a first end portion 200, a second end portion 210, and an intermediate portion 220. The chamber has an internal surface 230 and an external surface 240.

FIG. 2 also depicts the first end portion 200 of the chamber 190 and the second end portion 210 of the chamber 190 sealed to the external surface 140 of the vacuum tubing 30.

Absorbent material 300 is disposed between the internal surface 230 of the chamber 190 and the external surface 140 of the wall 550. The absorbent material 300 is adjacent to the one or more perforations 400.

Figure 3:
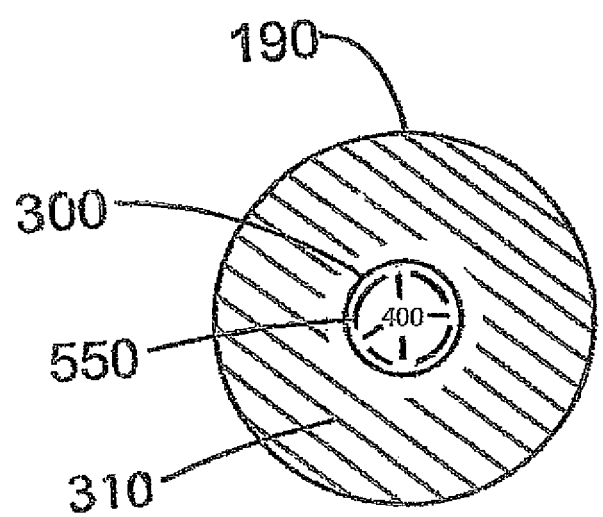
FIG. 3 illustrates a cross-sectional view of the embodiment of the invention shown in FIG. 2 hereof.

FIGS. 2 and 3 depict space between the one or more perforations 400 and the absorbent material 300 and space between the wall 550 and the absorbent material 300 to show the individual elements. In one embodiment of the invention, there is no space between the one or more perforations 400 and the absorbent material 300 nor is there space between the wall 550 and the absorbent material 300.

In one embodiment of the present invention, the absorbent material 300 comprises filter material. In another embodiment of the present invention, the absorbent material 300 comprises a liquid permeable barrier material effective for transferring fluids but not desiccant. The absorbent material 300 provides a means for wound leakage material to be transferred from one or more perforations 400 of the wall 550 and into the chamber 190 as the wound leakage material travels from the wound leakage source 20 towards the negative pressure source 10.

The wall 550 provides support such that the absorbent material 300 does not clog or occlude the application of negative pressure to the wound leakage source 20 from the negative pressure source 10. It is contemplated within the scope of this invention that the wall includes structures such as screens, various meshes, scaffolding, rods and bars.

FIG. 2 depicts a desiccant material 310 disposed between the absorbent material 300 and the internal surface 230 of the chamber 190. The desiccant material 310 absorbs the wound leakage material from the absorbent material 300. The absorption of wound leakage material by the desiccant material 310 allows the absorbent material 300 to transfer additional wound leakage material from the one or more perforations 400 as such material flows from the wound leakage source 20 toward the negative pressure source 10 along the wall 550 of the intermediate portion 120.

There are many different fabrication techniques to make the invention described and disclosed herein. As an example, chamber 190 may be fabricated and prepared for its intended purpose by using lengths of vacuum tubing having three diameters, the external surface 140 of innermost tubing 30 having a first outer diameter. A first short length of vacuum tubing having an inner diameter approximately equal to the first outer diameter is threaded onto tubing 30 between the intermediate portion 120 and the first end 100 thereof, that is, between perforations 400 in wall 550 and tubing clamp 70, forming thereby a fluid seal with tubing 30. A second length of vacuum tubing having an inner diameter approximately equal to the outer diameter of the first short length of vacuum tubing, and having a length spanning the approximate distance between the first end 100 and the second end 110 of tubing 30, is threaded over tubing 30 and onto the first short length of tubing, forming thereby a fluid seal at one end of intermediate portion 120 corresponding to first end portion 200 of chamber 190. The open end of the second tube is filled with absorbent material 300. A second length of vacuum tubing having an inner diameter approximately equal to the first outer diameter is threaded onto tubing 30 between the intermediate portion 120 and second end 110 thereof, forming thereby a fluid seal at the other end of intermediate portion 120 corresponding to second end portion 210 of chamber 190. If the diameters of the tubing do not provide sufficient fluid and vacuum seals, a silicone or other sealing composition can provide additional sealing capability.

In one embodiment of the present invention, the vacuum tubing is flexible. In another embodiment of the present invention the chamber is flexible. In yet another embodiment of the present invention the chamber is cylindrical and having an axis along said tubing.

In one embodiment of the present invention, the one or more perforations 400 are disposed circumferentially around the wall 550. In another embodiment of the present invention, the chamber 190 is disposed circumferentially around the wall 550. In yet another embodiment of the present invention, the absorbent material 300 is disposed circumferentially around the external surface 140 of the wall 550. It is contemplated within the scope of the present invention that the individual size of the one or more perforations range from nanometers to multiple centimeters in length and width.

FIG. 3 depicts a cross sectional view of an embodiment of the wound leakage collection chamber of the present invention. The wall 550 has one or more perforations 400, which allow for the flow of wound leakage material (not depicted) from the inside to the outside of the wall 550 and then to the absorbent material 300. Wound leakage material flows from the absorbent material 300 to the desiccant material 310, which is encased by the chamber 190.

Any number of negative pressure sources are contemplated within the scope of this invention including a negative pressure sources that are battery powered, alternating current powered or manually powered.

It is believed that the apparatus of the present invention, and many of its attendant advantages will be understood by the foregoing description. It is also believed that it will be apparent that various changes may be made in the form, construction, and arrangement of the components thereof without departing from the scope and spirit of the invention or without sacrificing all of its material advantages. The forms herein before described, being merely exemplary and explanatory embodiment thereof. It is the intention of the following claims to encompass and include such changes.

What is claimed is:

1. A wound leakage containment device comprising: substantially hollow vacuum tubing having a wall, said wall having an external surface, an internal surface, a first end in fluid communication with a source of negative pressure, a second end in fluid communication with and directly connected to a source of wound leakage, and a perforated portion between the first end and the second end having one or more perforations extending through the wall between the internal surface and the external surface, the perforations being effective for permitting wound leakage to pass through the wall of said substantially hollow vacuum tubing responsive to negative pressure; a chamber for enclosing and maintaining a vacuum around the external surface of the perforated portion of said substantially hollow vacuum tubing; an absorbent material disposed within said chamber adjacent to the external surface of the perforated portion of said substantially hollow vacuum tubing; and one or more vapor-permeable plugs disposed in the internal surface of said substantially hollow vacuum tubing between the first end and the perforated portion thereof.

2. The device of claim 1, wherein said vacuum tubing is flexible.

3. The device of claim 1, wherein said chamber is flexible.

4. The device of claim 1, wherein said chamber is cylindrical and having an axis along said vacuum tubing.

5. The device of claim 1, wherein said fluid absorbent material comprises filter material.

6. The device of claim 1, wherein the absorbent material comprises a liquid permeable barrier material effective for transferring fluids but wherein the absorbent material is not desiccant.

7. The device of claim 1, further comprising desiccant disposed within said chamber and separated from the perforated portion of said vacuum tubing by said absorbent material.

8. The device of claim 1, further comprising a first vacuum line connection for separating said vacuum tubing from the source of negative pressure.

9. The device of claim 1, further comprising a second vacuum line connection for separating said vacuum tubing from the source of wound leakage.

10. The device of claim 9, further comprising a second tubing clamp disposed on the vacuum tubing between said chamber and said second vacuum line connection.

11. The device of claim 1, wherein the one or more plugs is liquid-impermeable.

12. The device of claim 1, wherein the negative pressure source is powered by any means including battery power, alternating current power, or manual power.

13. The device of claim 1, further comprising a vacuum gauge.

14. A method for containing leakage from a wound, comprising: applying a vacuum from a source of negative pressure to a first end of a substantially hollow tube having a first end and a second end, and a wall having an interior and an exterior surface, the second end being in fluid communication with directly connected to a source of wound leakage; collecting wound leakage flowing through the substantially hollow tube responsive to vacuum through one or more perforations in a portion of the wall of the substantially hollow tube extending therethrough, forming a perforated portion having an internal surface and an external surface, the external surface thereof being in contact with absorbent material disposed in a chamber enclosing and maintaining a vacuum around the exterior surface of the perforated portion of the substantially hollow tube; and one or more vapor-permeable plugs disposed within the substantially hollow tube between the one or more perforations and the source of negative pressure.

15. The method of claim 14, wherein the tube is flexible.

16. The method of claim 14, wherein the chamber is flexible.

17. The method of claim 16, wherein the chamber is cylindrical and having an axis along the tube.

18. The method of claim 14, wherein the absorbent material comprises filter material.

19. The method of claim 14, wherein the absorbent material comprises a liquid permeable barrier material effective for transferring fluids but not desiccant.

20. The method of claim 14 further comprising desiccant material disposed within the chamber and separated from the perforated portion of the tube by the absorbent material.

21. A wound leakage containment device comprising:
  a.) a substantially hollow conduit section having a conduit wall, the conduit wall having an external surface, an internal surface, the internal surface defining a passageway extending from a first conduit termination to a second conduit termination, the passageway containing no absorbent material or desiccant, the first conduit termination being configured for fluid communication with a source of negative pressure, the second conduit termination being configured for fluid communication with a source of wound leakage, and the substantially hollow conduit section containing a perforated portion, the perforated section having one or more perforations extending through the conduit wall, the perforations being configured to permit wound leakage fluid to flow through said perforations to the external surface;
  b.) a chamber sealingly enclosing the perforated portion for enclosing and maintaining a vacuum around the external surface of the perforated portion;
  c.) an absorbent material disposed within the chamber adjacent to the external surface of the perforated portion; and
  d.) one or more vapor-permeable plugs disposed in the passageway between the first conduit termination and the perforated portion.

22. The device of claim 21 wherein wound leakage material comprises a vapor portion and wherein the conduit section is configured such that the source of negative pressure causes the vapor portion to pass from the second conduit termination through the passageway and the first conduit termination without passing through the absorbent material.

23. The device of claim 21 further comprising desiccant disposed within said chamber and configured to absorb wound leakage material fluid from said absorbent material.

24. The device of claim 23 wherein wound leakage material comprises a vapor portion and wherein the conduit section is configured such that the source of negative pressure causes the vapor portion to pass from the second conduit termination through the passageway and the first conduit termination without passing through the desiccant.

25. The device of claim 21 wherein the chamber extends from a first conduit location to a second conduit location, the first conduit location being spaced from the source of negative pressure and the second conduit location spaced from the source of wound leakage.

26. The device of claim 21 wherein the conduit section comprises a tubing section.

27. The device of claim 26 wherein the conduit section comprises a vacuum tubing section.

28. The device of claim 21 wherein the perforated portion comprises a plurality of perforations extending through the conduit wall.

29. The device of claim 28 wherein the perforated portion comprises a plurality of perforations extending circumferentially about the conduit wall.

30. The device of claim 21 wherein the absorbent material adjacent to the external surface of the perforated portion comprises filter material.

31. The device of claim 21 wherein the absorbent material adjacent to the external surface of the perforated portion is not desiccant.

32. The device of claim 21 wherein the absorbent material adjacent to the external surface of the perforated portion comprises a liquid permeable barrier material effective for transferring fluids.

33. The device of claim 21 wherein the first conduit termination further comprises a first vacuum line connector for connecting the conduit section to and separating the conduit section from the source of negative pressure.

34. The device of claim 21 wherein the second conduit termination further comprises a second vacuum line connector for connecting the conduit section to and separating the conduit section from the source of wound leakage.

35. The device of claim 21 wherein the one or more vapor-permeable plugs disposed in the passageway are liquid-impermeable.

36. The device of claim 21 wherein the source of negative pressure comprises a vacuum pump.

37. The device of claim 21 further including the source of negative pressure.

* * * * *